United States Patent [19]

Holub

[11] Patent Number: 5,281,394
[45] Date of Patent: Jan. 25, 1994

[54] DATA COLLECTION AND SAMPLE HANDLING APPARATUS

[75] Inventor: John M. Holub, Buffalo Grove, Ill.

[73] Assignee: ICN Biomedicals, Inc., Costa Mesa, Calif.

[21] Appl. No.: 384,298

[22] Filed: Jul. 21, 1989

[51] Int. Cl.$^5$ .......................................... G01N 21/00
[52] U.S. Cl. ................................. 422/65; 422/82.09; 436/48; 436/57; 436/172; 250/328
[58] Field of Search .............. 422/65, 68.1, 63, 82.05, 422/82.09, 73, 50; 436/47, 48, 57, 172; 250/328; 435/291, 300, 808

[56] References Cited

U.S. PATENT DOCUMENTS

| | | | |
|---|---|---|---|
| 3,271,574 | 9/1966 | Dawson et al. | 250/328 |
| 3,722,719 | 3/1973 | Frank | 250/328 |
| 3,723,736 | 3/1973 | Laney | 250/328 |
| 3,855,473 | 12/1974 | Burgess et al. | 250/328 |
| 3,883,742 | 5/1975 | Olson et al. | 250/328 |
| 3,890,505 | 6/1975 | Olson | 250/328 |
| 3,911,274 | 10/1975 | Roos et al. | 250/328 |
| 3,931,520 | 1/1976 | Bell et al. | 250/328 |
| 3,986,028 | 10/1976 | Byrd | 250/328 |
| 3,999,068 | 12/1976 | Stabile | 250/328 |
| 4,001,584 | 1/1977 | Mueller | 250/328 |
| 4,005,292 | 1/1977 | Oesterlin et al. | 250/364 |
| 4,035,642 | 7/1977 | Johnson, Jr. et al. | 250/328 |
| 4,119,850 | 10/1978 | Reddy et al. | 250/328 |
| 4,147,250 | 4/1979 | Schulz | 250/328 |
| 4,303,858 | 12/1981 | Östrup | 250/328 |
| 4,582,990 | 4/1986 | Stevens | 250/328 |
| 4,626,684 | 12/1986 | Landa | 250/328 |
| 4,924,093 | 5/1990 | Johnson et al. | 250/328 |

FOREIGN PATENT DOCUMENTS 0022988 4/1981 European Pat. Off. .

OTHER PUBLICATIONS

"Innovations", *Atomkernenergie-Kerntechnik*, vol. 44, No. 1, Jan. 1984, p. 94.

Primary Examiner—Robert J. Warden
Assistant Examiner—Theresa A. Trembley
Attorney, Agent, or Firm—Speckman, Pauley & Fejer

[57] ABSTRACT

A data collection and sample handling apparatus having a frame which supports a tray for holding a plurality of test containers. The tray has a plurality of through holes and each test container is mateable within a corresponding through hole. At least one detector assembly is used to detect data from the contents or sample contained within each test container. Each detector assembly is supported by the frame. The tray is positioned on a top of the frame such that at least one test container is exposed to each detector assembly while at least one other test container is isolated from the detector assembly. A drive mechanism automatically moves the tray with respect to the detector assemblies. The drive mechanism is also used to position each test container within a corresponding detector assembly.

28 Claims, 4 Drawing Sheets

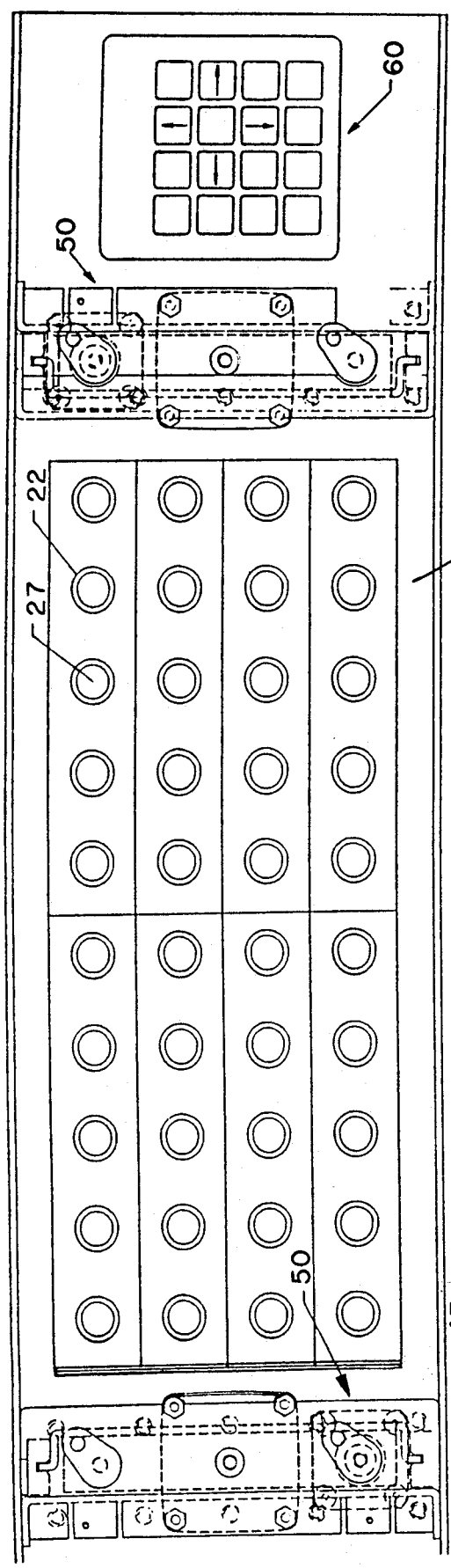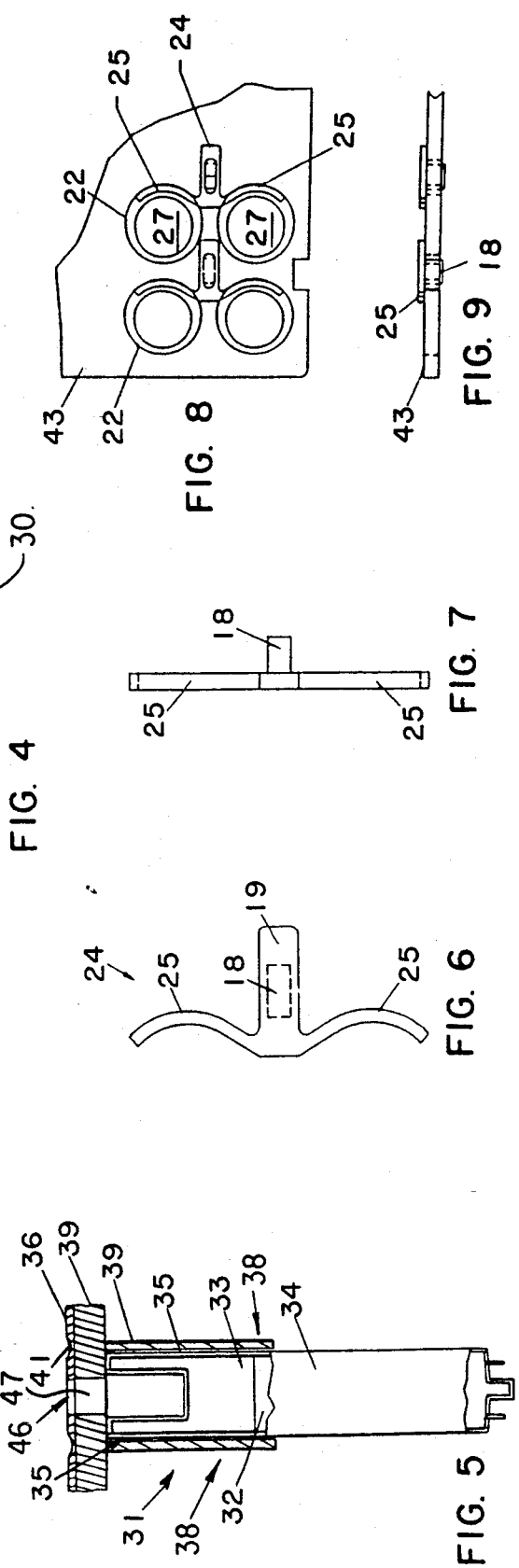

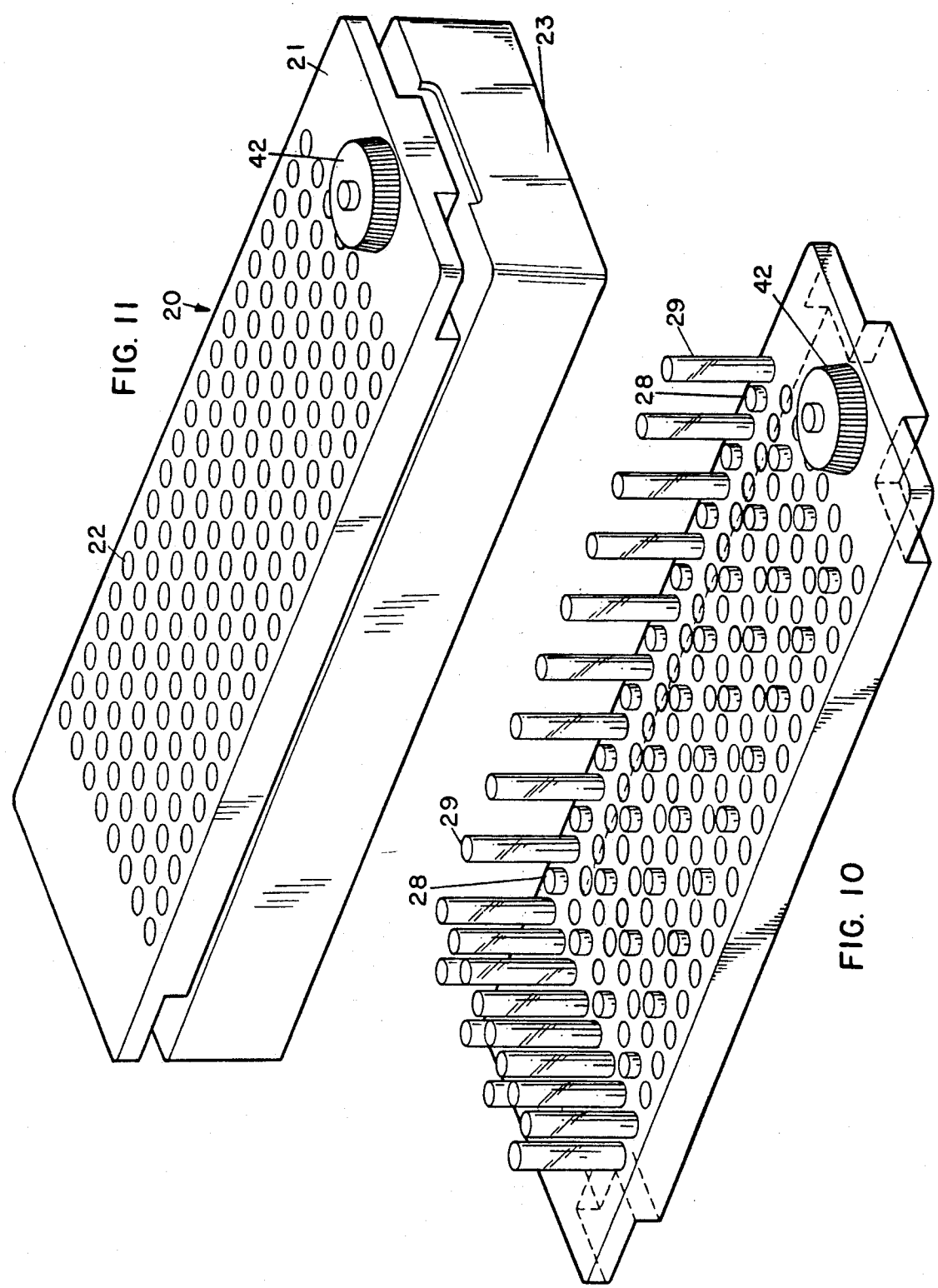

DATA COLLECTION AND SAMPLE HANDLING APPARATUS

BACKGROUND OF THE INVENTION

1. Field of the Invention

A data collection and sample handling apparatus having a frame, a tray for holding a plurality of test containers, a plurality of detector assemblies for detecting data from samples contained within the test containers, and a drive mechanism for moving the tray with respect to the detector assemblies.

2. Description of the Prior Art

Existing apparatuses for exposing a sample within a test tube or other test container to a detector assembly or other testing device include manual systems whereby a lab technician positions a first sample within the detector assembly, waits for the analyzing process to occur, removes the first test container and then repeats the process for succeeding test containers. In particular, gamma counting devices for analyzing blood samples, and the like, require a specific spacing between detector assemblies for accurate analysis, due to the laws of physics. The detector assemblies must be spaced a certain distance from each other to prevent radiation carry-over from one detector assembly to another. Other detection systems for various data collection unrelated to gamma counting exist.

For example, a sodium iodide detector assembly for analyzing blood samples by gamma counting requires a minimum spacing of approximately of 1½" between centers of detector assemblies. It is advantageous to space the detector assemblies as close together to minimize the size and thus cost of a collection and handling apparatus which accommodates multiple detector assemblies. In gamma counting devices used for analysis of blood samples, it is common to have approximately ⅛" of a shielding material, such as lead, between the detector assemblies.

Existing gamma counting devices which accommodate more than one sample or test container at a time require manual repositioning of the test containers. Such manual repositioning results in cumbersome lab procedures and inefficient use of skilled technician labor.

Some detector assemblies require extended time periods for detecting or collecting data. For example, using a gamma counter to analyze a blood sample requires approximately one minute to collect all of the necessary data. Conventional apparatuses can handle only relatively small amounts of samples thus analyzing 100 samples, for example, may take hours with conventional apparatuses, such as single detector systems.

The existing apparatuses used for analyzing samples, particularly for gamma counting of blood samples, have a need for an increase of samples analyzed per unit of time. Manual multi-detector systems exist for analyzing as many as 20 to 40 samples at a time. However, such multi-detector systems or apparatuses require manual loading and unloading. Such manual systems consume a relatively large amount of area to hold the test containers in trays and an operator must be in attendance at all times.

SUMMARY OF THE INVENTION

The data collection and sample handling apparatus of this invention can handle multiple test tubes or test containers, preferably about 160 test containers. In gamma counting, the spacing of test containers within a test container holder or tray is determined by the spacing of detector assemblies within the counting apparatus. For example, gamma counting related to blood samples requires detector assemblies which each occupy approximately 4 times the area occupied by a test tube. Thus, it is possible to construct a tray which accommodates 4 test tubes for each detector assembly.

By having an array of detectors, such as 40, 160 tubes can be placed within the test container holder. 40 samples can be counted by the detector assembly at a given time. Once the count time is complete, the test container holder can be repositioned so that a second test tube of the 4 test tubes of each section can be exposed to the detector assembly and counted. Such apparatus will allow samples to be analyzed within approximately 20 to 25% of the time required by a manual multi-detector system.

It is one object of this invention to provide a data collection and sample handling apparatus which increases the number of samples analyzed per unit of time.

It is another object of this invention to provide a data collection and sample handling apparatus having multiple detector assemblies for simultaneously analyzing multiple samples.

It is another object of this invention to provide a data collection and sample handling apparatus having a container holder which allows at least one test container of a group of 2 to 4 test containers to be exposed to a detector assembly while simultaneously isolating at least one other test container from the detector assembly.

It is still another object of this invention to provide a data collection and sample handling apparatus having a drive mechanism for moving a test container holder with respect to the detector assemblies and for positioning each of the test containers within the detector assemblies, in a rotational fashion.

In a preferred embodiment according to this invention, the data collection and sample handling apparatus has a frame which is used to support a tray for holding test containers. The tray has a plurality of through holes into which corresponding test containers mate and are secured. At least one detector assembly is used to detect data from sample contents of each test container. Each detector assembly is supported by the frame.

The test container holder or tray allows at least one active test container to be exposed to the detector assembly while simultaneously isolating at least one other idle test container from the detector assembly. The test container holder or tray preferably has approximately vertical through holes which are arranged in an array of columns and rows. In one embodiment of this invention, each test container holder or tray is divided into sections wherein each section houses 2 to 4 test containers. Each section of the tray preferably holds 4 test containers. The test container holder may comprise any reasonable number of sections, such as 2 to 100 sections, preferably 5 to 40 sections. Each section of the test container holder or tray corresponds to a detector assembly.

In one embodiment of this invention, the test containers can be fixed with respect to the tray so that the tray can be inverted to empty contents of the test containers or to clean the test containers without the test containers falling out of the tray. The test containers can be fixed with respect to the tray by having a container spring assembly which locks the test containers in position by abutting selected test containers. In one preferred embodiment of this invention, the container spring assembly comprises at least one arm having a shape compatible with the outside periphery of each test container. The arm is spring loaded to force and frictionally hold the selected test containers against the side of the tray. In another embodiment of this invention, the test containers are fixed with respect to the tray by having a plate with through holes corresponding to the through holes of the tray. The plate is laminated with an offset layer of a compressible material. The compressible material and the plate slide with respect to the tray and thus use friction to hold the test container between the compressible material and the tray. In yet another embodiment, each test container has a sleeve with a collar that fits within the through hole of the tray. The collar allows the sleeve to move within the through hole of the tray and the collar allows the sleeve and test container to vertically displace within the through hole of the tray.

In a preferred embodiment according to this invention, each test container comprises a test tube. The test tubes can have similar or different cross-sectional shapes which are compatible with the cross-sectional shape of the detector assembly. It is apparent that various detector assemblies can be used with the apparatus of this invention. In a preferred embodiment according to this invention, each detector assembly comprises a sodium iodide detector assembly. Such sodium iodide detector assemblies are used for gamma counting samples, such as blood samples and the like. Each sodium iodide detector preferably comprises a photo multiplier tube, sodium crystal material and an aluminum sheath around the crystal. The aluminum sheath is used to deflect light.

Each detector assembly is preferably mounted on the frame. Each detector assembly is isolated from each other by at least one layer of a shielding material which encases the detector assembly on all sides, including the top side of the detector assembly. The shielding material on the top side of the detector assembly has a through hole which accommodates the test container. The shielding material at the top side of each detector assembly is preferably positioned beneath the test container holder or tray. In a preferred embodiment of this invention, the through hole of the shielding material is sized and has a thickness which provides an angle that prevents idle test containers not within the detector assembly from being detected or counted by the detector assembly. The shielding material preferably comprises lead.

The data collection and sample handling apparatus also includes an automatic drive mechanism. In a preferred embodiment according to this invention, the automatic drive mechanism is connected to the test container holder or tray. It is apparent that the test container holder may comprise one or more separate trays, each having the through holes for accommodating test containers. In an embodiment having a plurality of trays, each tray is connected to the drive mechanism.

In another preferred embodiment according to this invention, the top, or cover, of the frame, which is used to cover the detector assemblies, is also used to retain each idle test container in an isolated position from the detector assembly, while the active container is exposed to the detector assembly. The cover preferably has a detent to retain each idle test container in an isolated position from the detector assembly and such detent also allows the test container to be lowered with respect to the detector assembly thus allowing the idle test container to contain a higher level of the sample without being detected by the detector assembly.

The drive mechanism moves the test container holder in a position where one of the test containers within each section can be inserted into the detector assembly. After a determined or programmed length of time, the drive mechanism removes a first test container from the detector assembly, shifts the test container holder or tray to a second position, then inserts a second test container into the detector assembly. Such process is repeated until all test containers within each section have been analyzed by the detector assembly. In one preferred embodiment of this invention, the drive mechanism is mounted to the frame, below the cover of the frame. In another preferred embodiment, the drive mechanism is mounted to the frame, above the cover of the frame.

In another preferred embodiment according to this invention, a computer is used to process data collected from the sample contents by the detector assemblies. The computer receives signals emitted from the detector assembly. Such signals represent data, such as qualitative and/or quantitative measurements taken from the sample contents. Such qualitative and/or quantitative measurements may include gamma counting.

In a preferred embodiment according to this invention, a preferred process for data collection and sample handling includes supporting a plurality of test containers in a test container holder and sectioning the test containers in at least one group of 2 to 4 of the test containers. One of the test containers is designated as an active test container and each remaining test container is an idle test container. Each active test container is exposed to a corresponding detector assembly while simultaneously isolating each of the idle test containers from the corresponding detector assembly. The test containers are then automatically rotated until each test container within each group is exposed to a corresponding detector assembly. Upon exposure to the detector assembly, data is read from the samples within each active test container. Such data can be emitted as a signal from the detector assemblies to a computer for processing the data.

BRIEF DESCRIPTION OF THE DRAWINGS

Further features of the invention will be apparent from the following more detailed description taken in conjunction with the drawings, wherein:

FIG. 4 is a top view of the drive means, detector means and computer means of the data collection and sample handling apparatus according to one embodiment of this invention;

FIG. 5 is a partial cross-sectional view of a detector assembly according to one embodiment of this invention;

FIG. 6 is a top view of the container spring means according to one embodiment of this invention;

FIG. 7 is a side view of the container spring means as shown in FIG. 6;

FIG. 8 is a top view of the container spring means and how it is positioned and operates with respect to the tray and the test containers according to one embodiment of this invention;

FIG. 9 is a side view of the container spring means as shown in FIG. 8;

FIG. 10 is a perspective view of the test container holding means with active and idle test containers according to one embodiment of this invention: and FIG. 11 is a perspective view of the test container holding means placed upon a tray stand according to one embodiment of this invention.

DESCRIPTION OF THE PREFERRED EMBODIMENTS

Figure 1:
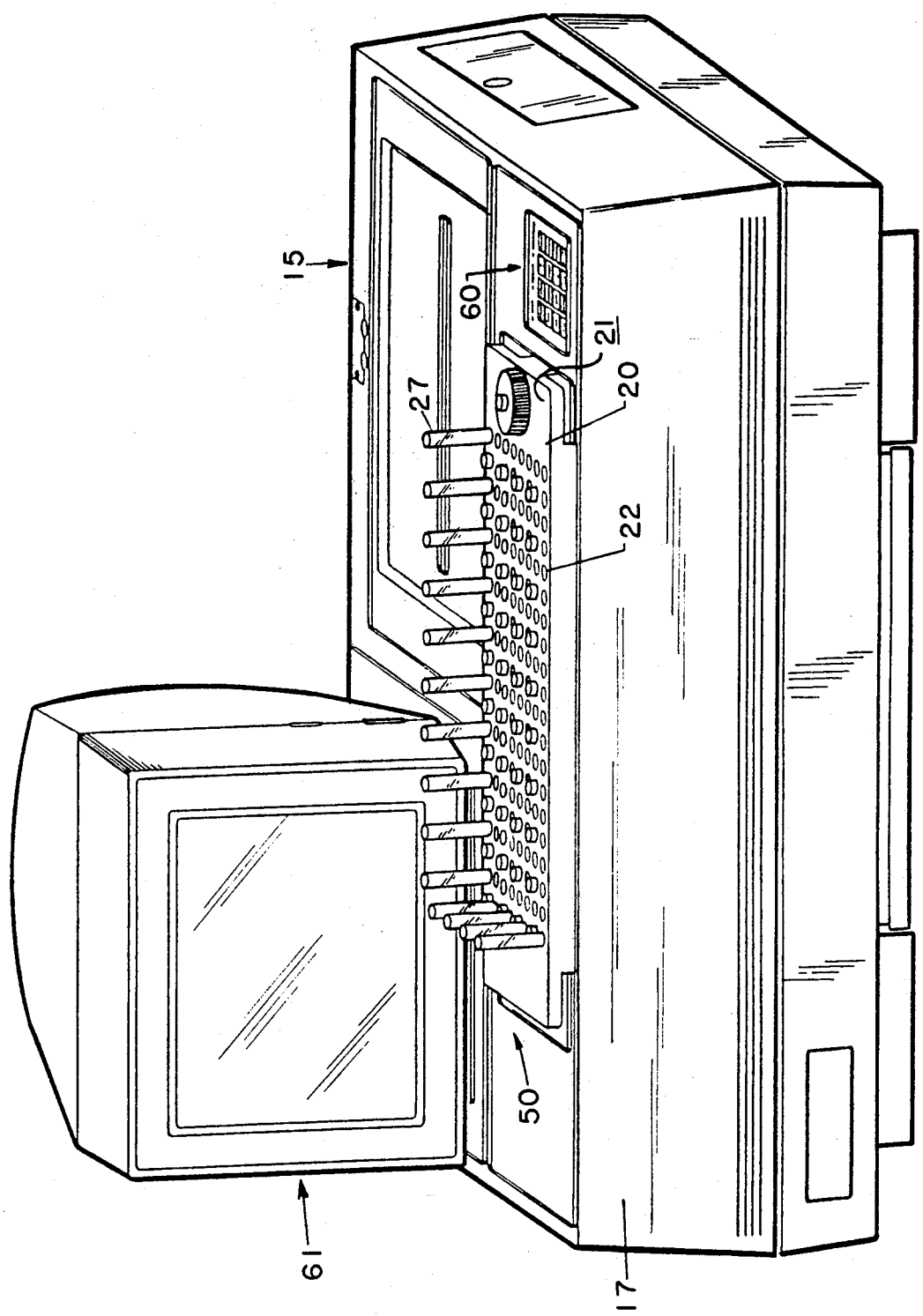
FIG. 1 is a perspective outline view of a data collection and sample handling apparatus according to one embodiment of this invention.

FIG. 1 shows a preferred embodiment of data collection and sample handling apparatus 15 which includes: frame 17; test container holding means 20; detector means 30 which are not shown in FIG. 1 but located beneath tray 21; drive means 50 which are not shown in detail in FIG. 1 but rather the general area of drive means is shown in FIG. 1; and computer means 60. In FIG. 1, computer means 60 is shown as a keypad and it is apparent that such keypad, as well as other components, can be connected to a local or remote computer. For drawing clarity purposes, FIG. 1 shows tray 21 having one lowered test container 27 and only one of three total standing or idle test containers 29 on the top row and left column of test containers 27.

Frame 17 can include a shell-type frame as shown in FIG. 1, a tubular frame or any other suitable frame known in the art. FIG. 1 shows a preferred embodiment of a shell-type frame which is aesthetically attractive and convenient for positioning the various elements of this invention. Frame 17 can be made from any suitable material such as metal, fiberglass, plastic or the like.

FIGS. 2-11 show various embodiments of test container holding means 20. Test container holding means 20 is supported by frame 17. FIG. 1 shows the general arrangement in which frame 17 supports test container holding means 20. However, it is apparent that other physical support arrangements can be used to accomplish adequate support of test container holding means 20.

In one preferred embodiment according to this invention, test container holding means 20 comprises tray 21 having a plurality of through holes 22. Through holes 22 are preferably positioned in an approximately vertical position and are also preferably arranged in an array of columns and rows, as shown in FIGS. 1, 2, 10 and 11. The vertical position of through hole 22 allows test container 27 to drop through tray 21 due to gravity forces. Test container holding means 20 further includes a plurality of test containers 27 which are each mateable with a corresponding through hole 22. In a preferred embodiment of this invention, each test container 27 is a test tube. It is apparent that other suitably shaped test containers can be used in this invention; however, a test tube is a commonly used type of test container within laboratories.

Tray 21 and through holes 22 provide for manual or automatic pipetting, water bathing or air incubating and counting. In a preferred embodiment of this invention, test container holding means 20 has at least one section 26, preferably multiple sections 26, each housing 2 to 4 test containers 27. In another preferred embodiment where relatively higher energy systems are used, detector assemblies 31 require greater spacing between each other and in such higher energy systems an array of 64 test containers 27, 8 columns and 8 rows, or more, occupies each section 26. Thus, each section 26 can house about 64 or more test containers 27. One test container 27 of each section 26 is an active test container 28 and each remaining test container 27 of section 26 is an idle test container 29. As shown in FIG. 10, active test container 28 is the test container which is inserted into detector assembly 31 for analyzing. Each idle test container 29 remains in an upright position. For drawing clarity purposes, FIG. 10 shows only the left column of sections 26 having one active test container 28 and three idle test containers 29. All idle test containers 28 are not shown in the remainder of tray 21 as shown in FIG. 10.

Figure 2:
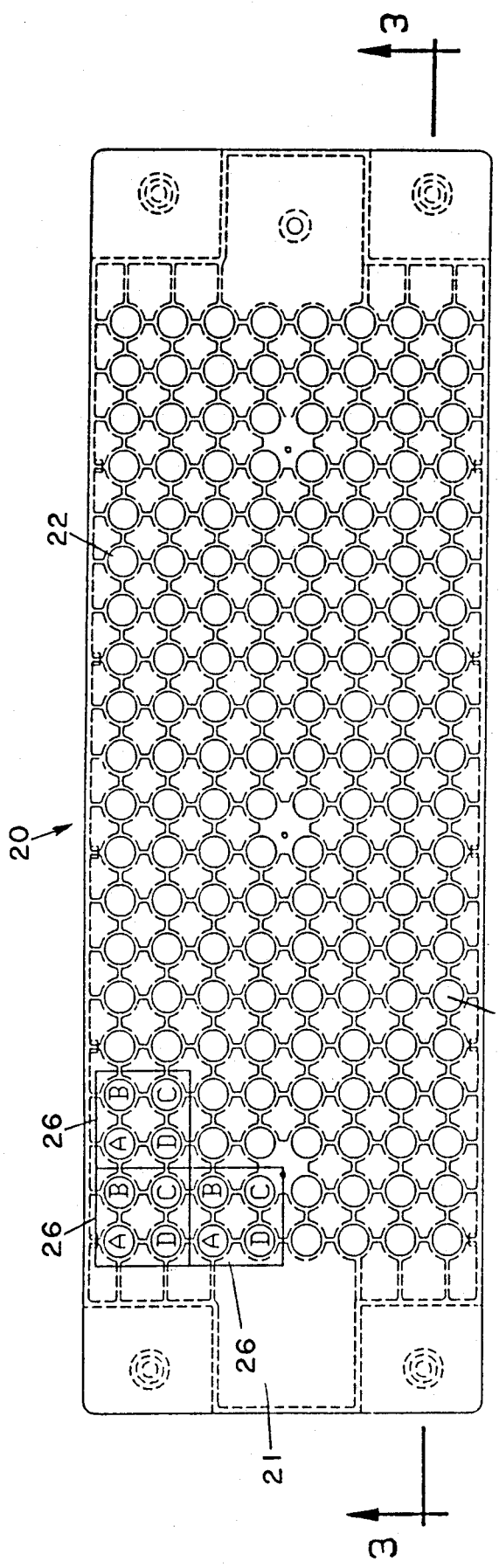
FIG. 2 is a top view of test container holding means according to one embodiment of this invention.
Figure 3:
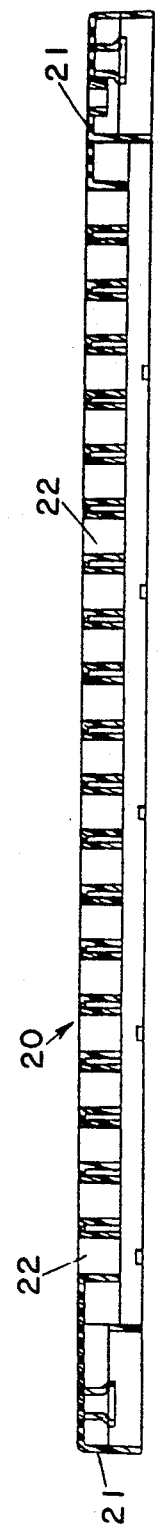
FIG. 3 is a cross-sectional side view along line 3—3, as shown in FIG. 2, of the test container holding means shown in FIG. 2.

FIG. 2 shows a preferred embodiment of this invention in which tray 21 has through holes 22 and is divided into sections 26, each having 4 test containers 27. One of the 4 test containers 27 fits within detector assembly 31 for analyzing. The remaining idle test containers 29 remain isolated from detector assembly 31. Each idle test container 29 remains above cover 36 of frame 17 by retaining means. In one preferred embodiment of this invention, the retaining means includes cover 36 having detents 41 for holding idle test containers 29.

Once the first active test container 28 has remained within detector assembly 31 for a determined or programmed period of time, tray 21 is lifted from cover 36. During the lifting process, all test containers 27 slide downward within through holes 22 until an upper lip of test container 27 or other holding means prevent each test container 27 from falling through the bottom of through hole 22. Tray 21 is then repositioned until the next test container 27 is positioned over detector assembly 31 such that the second test container 27 can become an active test container 28.

Thus, as shown in FIG. 2, section 26 has 4 test containers 27 labeled 27A, 27B, 27C, and 27D. For example, when tray 21 is first positioned, test container 27A is lowered into detector assembly 31 for a specified period of time. Once the time has expired, tray 21 is lifted causing all active test containers 28 to be raised from within corresponding detector assemblies 31. Tray 21 is then shifted to position test container 27B directly over detector assembly 31 so that test container 27B can be placed within detector assembly 31. Such process is repeated until test containers 27A, 27B, 27C and 27D have been analyzed within detector assembly 31. FIG. 2 shows tray 21 having 40 sections 26 and thus 160 total test containers 27. Thus 40 active test containers 28 can be analyzed at a given time. By moving tray 21, 160 total test containers 27 can be analyzed without switching tray 21. Tray 21 can have any suitable number of sections 26, such as 1 to 100 sections 26 and preferably 5 to 40 sections 26.

In one preferred embodiment according to this invention, detector means 30 detects data from sample contents of each active test container 28. In a preferred embodiment, detector means 30 includes a plurality of detector assemblies 31. The detector assemblies 31 are supported by frame 17 in any suitable manner familiar to the art. In a preferred embodiment of this invention, detector assembly 31 comprises a sodium iodide detector assembly. As shown in FIG. 5, each detector assembly 31 includes photo multiplier tube 32, sodium crystal material 33, aluminum sheath 34 and aluminum housing 35. Aluminum sheath 34 is positioned around sodium crystal material 33 is for deflecting light. It is apparent that detector assembly 31 may also comprise a photocell, photometer, fluorometer and the like.

Each detector assembly 31 is isolated from each other by having at least one layer of shielding material 39 encasing detector assembly 31 on all sides 38, including the cover top sides of detector assembly 31 36 and shielding material 39 have through holes 46 and 47, respectively, which align with and have a size corresponding to through hole 22 of tray 21. Through hole 46 and 47 allow active test container 28 to fit through cover 36 into detector assembly 31. Shielding material 39 at cover 36, over detector assembly 31, is preferably positioned beneath tray 21 or other test container holding means 20. Through hole 46 of shielding material 39 has a thickness and diameter or other dimensions calculated and sized to provide an angle that prevents or isolates each idle test container 29 from being detected or counted by detector assembly 31. The level of liquid or other sample within idle test container 29 is a parameter to consider in such calculation. Shielding material 39 preferably comprises lead.

Drive means 50 are used for automatically or manually moving test container holding means 20 with respect to detector means 30. Drive means 50 positions each test container 27 over detector assembly 31 such that test container 27 can be lowered into detector assembly 31 and become an active test container 28.

In one preferred embodiment according to this invention, drive means 50 includes a drive mechanism which is connected to tray 21 or other test container holding means 20. Drive means 50 rotate each test container 27 of each section 26 through each corresponding detector assembly 31. Drive means 50 can also include a timer for retaining active test container 28 within detector assembly 31 for a specified period of time. It is apparent that drive means 50 may also include manually raising, positioning and lowering tray 21 or other test container holding means 20. With such manual drive means 50, the drive mechanism is not an essential element of this invention.

Drive means 50 may include a gear mechanism, cams, and a motor for automatically moving tray 21 in a desired path. As shown in FIGS. 10 and 11, knob 42 is mechanically connected to a cam that is used to move tray 21. Drive means 50 can include any suitable drive mechanism familiar to the art for moving tray 21 in such path. Drive means 50 can be mounted to frame 17 below and/or above cover 36. In one preferred embodiment according to this invention, one tray 21 is connected to drive means 50. In another preferred embodiment, a plurality of trays 21 are each connected to drive means 50. It is apparent that multiple trays 21 can be used for positioning active test containers 28 within corresponding detector assemblies 31.

Test container holding means 20 can have test container spring means 24 slideably mounted on tray 21. Such container spring means 24 are used to lock each test container 27 with respect to tray 21. Such locked position of test containers 27 allows tray 21 to be inverted without test containers 27 falling from through holes 22.

In a preferred embodiment of this invention, container spring means 24 includes arm 25, as shown in FIGS. 6-9. Each arm 25 has base 19 with guide 18 which fits within a slot of a slideable plate 43 mounted a fixed distance beneath tray 21; such fixed distance is slightly greater than the thickness of either base 19 or arm 25. Slideably displacing plate 43 through contact between guide 18 and the side of a slot displaces base 19 and thus arm 25 of container spring means 24. It is apparent that plate 43 can be displaced relative to tray 21, in any direction in a plane approximately parallel to tray 21, by having a cam mechanism either directly in contact with plate 43 or attached to plate 43 through mechanical linkage. Arm 25 has a shape that is compatible with an outside periphery of each test container 27. In a locked position, arm 25 is capable of holding test container 27 against tray 21 so that friction between tray 21 and test container 27 retain test container 27 in a locked position with respect to tray 21. Container spring means 24 can have arms 25 selectively positioned for grasping or retaining specified test containers 27.

In another preferred embodiment, container spring means 24 includes a laminate attached to plate 43. The laminate preferably is of a compressible material, such as foam, rubber or the like, and has through holes slightly offset with respect to the through holes of the tray. Such offset arrangement frictionally holds test container 27 against tray 21 when plate 43 is slideably displaced with respect to tray 21. In yet another embodiment of this invention, test container 27 has a sleeve with a collar that mates with through hole 22 of tray 21. The collar allows the sleeve to vertically displace within through hole 2 and the collar retains test container 27 within through hole 22 when tray 21 is inverted.

In another preferred embodiment according to this invention, data collection and sample handling apparatus 15 further includes computer means 60 for processing the data obtained from the sample contents. Computer means 60 receives signals emitted by detector means 30 and processes such data into a readable output on monitor 61. The data can include quantitative and/or qualitative measurements, such as gamma radiation counting. It is apparent that computer means 60 is a preferred element of this invention but is not necessary for operation of the invention.

A process for data collection and sample handling according to one embodiment of this invention includes supporting a plurality of test containers 27 within test container holding means 20 and then sectioning test containers 27 in at least one group of 2 to 4 of the test containers 27. One of the test containers 27 of the group is an active test container 28 and each remaining test container 27 of the group is an idle test container 29. Active test containers 28 are then exposed to a corresponding detector assembly 31 while simultaneously isolating each idle test container 29 from the corresponding detector assembly 31. Test containers 27 are automatically rotated within each group for individual exposure to detector assembly 31. The data from the sample contents within each active test container 28 is read. Such data is emitted as a data signal from each detector assembly 31 to computer means 60 for processing the data.

It is apparent that the elements of this invention can be constructed in any suitable color and from metal, plastic or any other suitable material known in the art. For example, tray 21 can be painted black or made from a black material for optical isolation when using a photometer or other light detection or light sensitive apparatus.

While in the foregoing specification this invention has been described in relation to certain preferred embodiments thereof, and many details have been set forth for purpose of illustration it will be apparent to those skilled in the art that the invention is susceptible to additional embodiments and that certain of the details described herein can be varied considerably without departing from the basic principles of the invention.

I claim:

1. A data collection and sample handling apparatus capable of simultaneously analyzing a plurality of test containers, the apparatus comprising:
    a frame, a cover secured with respect to said frame;
    a tray supported by said frame, said tray having a plurality of arrays of tray through holes, each said tray through hole sized to accept one of a plurality of test containers;
    detector means for detecting data from a contents of the test containers, said detector means supported by said frame, said detector means comprising a plurality of detector assemblies, each said detector assembly corresponding to one of said arrays, said detector means exposing one of the test containers in each said array to said corresponding detector assembly while simultaneously isolating another of the test containers in each said array from said corresponding detector assembly;
    said cover having a cover through hole corresponding to each said array of tray through holes;
    drive means for selectively positioning said tray above said cover through holes with one of said tray through holes of each said array aligning above each said corresponding cover through hole allowing one test container in each said array to lower into said corresponding detector assembly.

2. An apparatus according to claim 1 wherein said tray through holes are approximately vertical and arranged in columns and rows.

3. An apparatus according to claim 1 wherein said tray has 2 to 64 said tray through holes within each said array.

4. An apparatus according to claim 3 wherein each said array has 4 said tray through holes.

5. An apparatus according to claim 1 wherein said tray further comprise test container spring means slidably mounted on said tray, and in a locked position said test container spring means abutting the test containers and securing selected said test containers with respect to tray.

6. An apparatus according to claim 5 wherein said test container spring means further comprise at least one arm having a shape compatible with an outside periphery of each said test container, said arm capable of holding said test container against said tray.

7. An apparatus according to claim 1 wherein each said test container comprises a test tube.

8. An apparatus according to claim 1 wherein each said detector assembly comprises a sodium iodide detector assembly.

9. An apparatus according to claim 8 wherein said sodium iodide detector assembly comprises a photo multiplier tube, sodium crystal material and an aluminum sheath around said crystal for deflecting light.

10. An apparatus according to claim 1 further comprising each said detector assembly mounted on said frame, each said detector assembly isolated from each other by at least one layer of a shielding material encasing each said detector assembly on all sides said shielding material having a shielding through hole on a top side of said detector assembly aligning with said cover through hole to accommodate said test container.

11. An apparatus according to claim 10 wherein said shielding material at said side of said detector assembly top and over said detector assembly is positioned beneath said tray.

12. An apparatus according to claim 10 wherein said shielding through hole and a thickness of said shielding is sized to provide an angle that prevents an idle test container of the test containers from being detected by said corresponding detector assembly.

13. An apparatus according to claim 10 wherein said shielding material further comprises lead.

14. An apparatus according to claim 1 wherein each said detector assembly is mounted on said frame;
    each said array houses 2 to 64 of the test containers wherein one said test container of each said array is an active test container and each of the remaining test containers of each said array is an idle test container; and
    said cover covers with said detector assembly, said cover having retaining means for retaining each said idle test container in a position isolated from said corresponding detector assembly, and said active container being exposed to said corresponding detector assembly.

15. An apparatus according to claim 14 wherein said retaining means further comprise said cover having a detent compatible with a bottom of each said idle test container.

16. An apparatus according to claim 14 further comprising 4 said test containers.

17. An apparatus according to claim 14 wherein said drive means moves said tray allowing each of the test containers of each said array to rotate through said corresponding detector assembly.

18. An apparatus according to claim 17 further comprising timing means for maintaining each said active test container within said corresponding detector assembly for a determined length of time.

19. An apparatus according to claim 14 wherein said tray has 1 to 100 said arrays.

20. An apparatus according to claim 19 further comprising 5 to 40 said arrays.

21. An apparatus according to claim 14 wherein said drive means is mounted to said frame below said cover.

22. An apparatus according to claim 14 wherein said drive means is mounted to said frame above said cover.

23. An apparatus according to claim 1 further comprising computer means for processing data from the contents of said plurality of test containers and said computer means receiving signals emitted by said detector means.

24. An apparatus according to claim 1 wherein said drive means further comprise an automatic drive mechanism connected to said tray.

25. An apparatus according to claim 1 wherein said tray is connected to said drive means.

26. In a data collection and sample handling apparatus having a frame, detector means mounted on said frame having a cover, said detector means for detecting data from contents of a plurality of test containers, the improvement comprising:
    test container holding means supported by the frame, said test containers holding means comprising a plurality of arrays of through holes, each of said test containers mateable with a corresponding said through hole, said cover having at least one cover through hole for each said array of through holes, drive means for selectively positioning said test container holding means above said cover through holes with one of said through holes of each said array aligning above a corresponding said cover through hole allowing one of the test containers of each said array to lower into a corresponding detector of said detector means.

27. A process for data collection and sample handling comprising the steps of:

supporting a plurality of test containers in a test container holder;

sectioning the test containers in a plurality of arrays of 2 to 64 of the test containers wherein one of the test containers of each said array is an active test container and each of the remaining test containers of each said array is an idle test container;

lowering each of the active test containers within a through hole of a cover over a plurality of detector assemblies and into each of the corresponding detector assemblies, each said through hole corresponding to one of said detector assemblies, while simultaneously isolating each of the idle test containers from the corresponding detector assembly;

rotating by sequentially positioning each of the test containers of each said array for exposure to the corresponding detector assembly; and reading data from contents within each of the active test containers.

28. A process according to claim 27 further comprising the step of emitting a data signal from each of the detector assemblies to a computer for processing the data.

* * * * *